United States Patent [19]

Khoobiar

[11] 4,271,040

[45] Jun. 2, 1981

[54] CATALYST AND PROCESS FOR PRODUCING METHACRYLIC ACID

[75] Inventor: Sargis Khoobiar, Kinnelon, N.J.

[73] Assignee: Halcon Research and Development Corp., New York, N.Y.

[21] Appl. No.: 81,406

[22] Filed: Oct. 3, 1979

Related U.S. Application Data

[63] Continuation-in-part of Ser. No. 973,354, Dec. 26, 1978, Ser. No. 972,745, Dec. 26, 1978, Ser. No. 972,743, Dec. 26, 1978, Ser. No. 973,495, Dec. 26, 1978, Ser. No. 27,632, Apr. 6, 1979, Ser. No. 27,633, Apr. 6, 1979, Ser. No. 27,634, Apr. 6, 1979, Ser. No. 27,635, Apr. 6, 1979, and Ser. No. 47,860, Jun. 12, 1979.

[51] Int. Cl.$^3$ .................. B01J 27/18; B01J 23/28; B01J 23/18
[52] U.S. Cl. .................... 252/437; 562/535
[58] Field of Search .................... 252/437; 562/535

[56] References Cited

U.S. PATENT DOCUMENTS

| | | | |
|---|---|---|---|
| 3,761,516 | 9/1973 | Khoobiar | 252/437 X |
| 3,965,163 | 6/1976 | Oda et al. | 252/437 X |
| 3,976,688 | 8/1976 | Akiyama et al. | 252/437 X |
| 3,998,877 | 12/1976 | Oda et al. | 252/437 X |
| 4,017,423 | 4/1977 | White et al. | 252/437 |
| 4,110,369 | 8/1978 | White et al. | 252/437 X |

*Primary Examiner*—Carl F. Dees
*Attorney, Agent, or Firm*—William C. Long; David Dick; Harold N. Wells

[57] ABSTRACT

A catalyst composition useful for the oxidation of unsaturated aldehydes, particularly the oxidation of methacrolein to produce methacrylic acid, comprises the combination of oxides of molybdenum, copper, phosphorus, antimony, and cesium and/or calcium and optionally may include one or more of the elements Ni, Zn, Ru, Rh, Pd, Pt, As, K, Rb, Sr, Ba, Cr, V, Nb, W, Mn, Re, and rare earth metals including La.

19 Claims, No Drawings

CATALYST AND PROCESS FOR PRODUCING METHACRYLIC ACID

CROSS-REFERENCE TO OTHER APPLICATIONS

This is a continuation-in-part of U.S. Ser. Nos. 973,354, 972,745, 972,743 and 973,495, all filed Dec. 26, 1978, 027,632, 027,633, 027,634, and 027,635, all filed Apr. 6, 1979, and U.S. Ser. No. 047,860 filed June 12, 1979.

PRIOR ART

This invention relates to a process and catalyst for the vapor-phase oxidation with molecular oxygen of methacrolein to methacrylic acid.

It is well known that unsaturated acids, such as acrylic acid and methacrylic acid, can be produced by the vapor-phase oxidation of the corresponding unsaturated aldehydes by means of molecular oxygen in the presence of a suitable oxidation catalyst. A variety of catalyst compositions have been proposed for this purpose. Many such compositions comprise the oxides of molybdenum and phosphorus in association with the oxides of various other elements, both metallic and non-metallic. Of interest is U.S. Pat. No. 3,395,178 which discloses a preferred molybdenum-phosphorus atomic ratio of 10:1 which is considered to be optimum for a catalyst consisting only of those two elements and disposed on a silicon carbide support. Also, British Pat. No. 1,498,595 indicates that phosphorus is effective in molybdenum-vanadium-phosphorus-cerium catalysts and that with a ratio of Mo:P greater than 12:3 the activity is decreased. However, in the molybdenum-phosphorus-vanadium-alkali metal catalyst of U.S. Pat. No. 4,075,244, the phosphorus content was varied between 0.5 and 3 ( relative to $Mo_{12}$) and no particular significance was noted.

British Pat. No. 1,430,337 and U.S. Pat. No. 4,000,088 propose the use of a catalyst composition in which the oxides of molybdenum and phosphorus are combined with the oxides of antimony, and copper and optionally with chromium. The catalyst does not contain cesium or calcium.

U.S. patents disclosing related catalysts which may contain cesium and calcium include U.S. Pat. Nos. 4,051,179, 4,042,533, and 4,042,625. In '179 the basic constituents are molybdenum, phosphorus, and arsenic. Copper and vanadium are treated as alternatives and while an alkali metal must be included, antimony and calcium are considered optional. In '533 molybdenum, tungsten and vanadium are required, while copper, phosphorus, and the alkali and alkaline earth elements are optional and antimony is lacking. In '625, magnesium and the alkali metals are added to molybdenum-phosphorus catalysts, while calcium is optional and copper and antimony are lacking. Examples of the catalyst include phosphorus levels of 1, 2, and 3 relative to $Mo_{12}$, but no particular significance was noted.

In U.S. Pat. No. 4,045,478 the use of calcium in molybdenum-phosphorus catalysts is taught. The catalyst lacks copper and the alkali metals while antimony is considered to be only an optional ingredient.

U.S. Pat. No. 3,976,688 teaches a molybdenum-phosphorus catalyst containing an alkali metal and a group of optional elements which include barium, but not calcium. Copper and antimony are lacking.

The catalyst disclosed in U.S. Pat. No. 4,042,533 also contains rhenium as an optional ingredient. Still another prior art patent disclosing the use of rhenium as an optional ingredient is U.S. Pat. No. 3,956,378. While this catalyst requires the presence of molybdenum and antimony, it lacks the alkali and alkaline earth metals and copper and phosphorus are only optional ingredients.

Many other elements have been used in catalysts for preparation of methacrylic acid by oxidation of methacrolein. U.S. patents which disclose the use of elements of interest with respect to the present invention include U.S. Pat. Nos. 4,001,316; 4,072,708; 4,138,365; 3,557,199; and 3,985,680. In these patents, as well as those previously mentioned, the catalysts differ from those to be disclosed hereinafter. The prior art catalysts generally are found to require elements not included in the catalysts of the present invention or some of the essential elements of the present catalysts are lacking in prior art catalysts.

It has been found that catalysts for oxidation of methacrolein to methacrylic acid have the characteristic property of remaining stable for a period of time and then, without warning, of beginning a rapid decline in activity. Consequently, an increase in the useful activity of such catalysts has been sought.

Despite the many disclosures of the prior art, an improved catalyst of this type is not developed merely by randomly selecting a group of the many elements which have been disclosed. Small changes in composition may be very important in achieving improved catalyst performance and particularly in optimizing the catalyst composition to suit, not only a specific reaction, but the desired operating conditions also. The point is well illustrated by the improved catalyst formulations to be described hereinafter.

SUMMARY OF THE INVENTION

It has been discovered that when using the catalysts to be described to produce methacrylic acid by vapor phase oxidation of methacrolein, it is possible to achieve both high activity and high selectivity for extended periods of time. Broadly, the catalyst composition comprises oxides of molybdenum, copper, phosphorus, antimony, and cesium and/or calcium and the composition may include one or more elements of Ni, Zn, Ru, Rh, Pd, Pt, As, K, Rb, Sr, Ba, Cr, V, Nb, W, Mn, Re, and rare earth metals including La.

The catalyst composition used in the process of the invention also may be expressed by the following general formula:

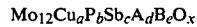

$$Mo_{12}Cu_aP_bSb_cA_dB_eO_x$$

wherein A is cesium and/or calcium and B is Ni, Zn, Ru, Rh, Pd Pt, As, K, Rb, Ca, Sr, Ba, Cr, V, Nb, W, Mn, Re, and rare earth metals including La, and where a-e and x indicate the atomic ratio of each component and, when a is 0.05-3, b is 0.1-5, c is 0.01-1, d is 0.1-3, e is 0-3, preferably 0.01-3, and x has a value which is determined by the valence and proportions of the other elements in the catalyst. Preferably, b will be 0.5-3, more preferably 1-2, and most preferably about 1.2-1.8.

Specific embodiments of catalysts according to the invention include catalysts containing cesium or calcium, alone or with rhenium, according to the following formulas: $Mo_{12}Cu_aP_bSb_cCs_dO_x$ or $Mo_{12}Cu_aP_bSb_cCa_dO_x$; where a-d and x have the range of values given above with the exception that b=1-2, preferably 1.2-1.8, and most preferably b=1.3=1.7; and $Mo_{12}Cu_aP_bSb_cCs_dRe_eO_x$ or $Mo_{12}Cu_aP_bSb_cCa_dRe_eO_x$ where a-e and x have the range of values given above with the exception that b=1-2, preferably 1.2-1.8, and most preferably b=1.3-1.7. Still another catalyst of the invention is represented by the formula $Mo_{12}Cu_aP_bSb_cCa_dW_eO_x$, again where a-e and x have the values given above with the exception that b=1-2, preferably b=1.2-1.8.

When such a catalyst as has been described is in contact with a vapor-phase mixture of methacrolein, molecular oxygen, steam, and nitrogen at typical temperatures in the range of 250°-400° C. and pressures in the range of 0-5 atmospheres, excellent activity and selectivity to the production of methacrylic acid is obtained for extended periods of time.

DESCRIPTION OF THE PREFERRED EMBODIMENTS

Catalyst Composition and Preparation

The catalyst of the invention comprises oxides or oxygen-containing compounds of molybdenum, copper, phosphorus, antimony, and cesium and/or calcium and optionally may include members of a group of elements to be named. The catalyst may be represented by the general formula:

$$Mo_{12}Cu_aP_bSb_cA_dB_eO_x$$

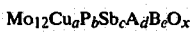

wherein A is cesium and/or calcium and B is Ni, Zn, Ru, Rh, Pd, Pt, As, K, Rb, Sr, Ba, Cr, V, Nb, W, Mn, Re and rare earth metals including La, and where a-e and x indicate the atomic ratio of each component relative to $Mo_{12}$ and, when a is 0.05-3, b is 0.1-5, c is 0.01-1, d is 0.1-3, e is 0-3, preferably 0.01-3, x is a value determined by the valence and proportions of the other elements in the catalyst. Preferably, b will be 0.5-3, more preferably 1-2, and most preferably about 1.2-1.8. Preferred catalysts include those in which component B is tungsten or rhenium. Other elements, which may be included in minor amounts in the catalyst formulation in order to promote catalyst activity or selectivity and without losing the advantages to be shown for the general formula, are considered to be within the scope of the invention. The catalyst composition may be regarded either as a mixture of oxides of the named elements or as oxygen-containing compounds of the elements or both. As prepared and/or under reaction conditions, the catalyst may contain either or both forms and both are intended to be included within the phrase "mixtures of oxides."

The catalyst composition is preferably used in unsupported form, e.g. in the form of pellets or other like compressed shapes of various sizes, although conventional supports could be employed instead. The composition may be formed in conventional manner using techniques well known to persons skilled in the art. For example, compounds of molybdenum, copper, phosphorus, antimony, cesium, and rhenium are dissolved in a small amount of water or other solvent, and the solutions are then combined and evaporated to dryness, e.g. in a rotary dryer. The several components can be introduced into solution in the form of various salts or other compounds of convenient types and no specific form for the catalyst precursors is necessary. The use of ammonium salts, halides e.g. chlorides, nitrates or acid forms of the elements, e.g. phosphoric acid, are, however, particularly suitable. Preferably, however, aqueous solutions are employed and water-soluble forms of the elements are used. In some cases the solutions may have acids and/or bases added to them to facilitate dissolution of the catalyst precursors. For example, acids such as hydrochloric or nitric acid, or bases such as ammonium hydroxide, can be used as desired. The resulting powder from the evaporation is then thoroughly dried and preferably screened to eliminate large particles which make it difficult to produce uniform compressed shapes, such as pellets. Typically, the powder is passed through a 20-mesh screen. The powder is then mixed with an organic binder which can be of any conventional type, such as polyvinyl alcohol, and the mixture is thoroughly dried and again screened, typically to provide a 20-60 mesh size. The dried mixture is then preferably combined with a lubricant, again of any conventional type, such as stearic acid or graphite, and compressed into the desired shape, e.g. pelletized, the compressed shapes typically having heights and diameters of 1/16 inch to ⅜ inch. Finally, the thus produced catalyst composition is activated at high temperature for a prolonged period in accordance with conventional practice in this art. For example, the pellets are placed in an oven or kiln, or in a tube through which air is passed, at an elevated temperature (e.g. 300°-500° C., preferably 325°-450° C.) for at least ten hours. In a particularly preferred activation step, the temperature is raised at the rate of 20° C. per hour to a maximum of 420° C., preferably 320°-400° C., and this temperature is maintained for 8 hours.

It will be understood that the foregoing description regarding preparation of the catalyst in a form suitable for use in a vapor-phase oxidation reaction is merely illustrative of many possible preparative methods, although it is a particularly suitable method and is preferred.

Methods of Operation

The catalysts described are generally useful for the production of unsaturated acids by oxidation with molecular oxygen of unsaturated aldehydes, although the reaction of methacrolein to form methacrylic acid is of particular interest. Other possible starting materials are the monoethylenically unsaturated aliphatic monoaldehydes of from 3 to 6 carbon atoms, such as acrolein, crotonaldehyde, 2-methyl-2-butenal, and the like, or mixtures thereof.

The reaction in which the catalyst compositions of this invention are of particular utility and in which they provide high conversions and selectivities involves contacting the catalyst with methacrolein and oxygen in the vapor phase, preferably also in the presence of steam and diluents. When the catalyst of this invention is used in the vapor-phase oxidation of methacrolein to form methacrylic acid, the oxidation conditions employed are those generally associated with this reaction, although it is preferred that the molar ratio of oxygen to methacrolein should be kept at a high value near the flammable range. Once reaction is begun, it is self-sustaining because of its exothermic nature. A variety of reactor types may be employed such as fluid or fixed bed types, but reactors having the catalyst disposed inside a multiplicity of heat exchanger tubes are particularly useful and convenient.

The gaseous feed to the reactor contains appropriate concentrations of methacrolein, oxygen and steam and usually an inert gas is also present, such as nitrogen and the like. The oxygen is usually added as such or as air, which may be enriched with oxygen. As mentioned, conventional oxidation conditions can be employed but it is a feature of the catalyst of this invention that methacrolein can be present in concentrations of more than 5 up to about 20 volume percent of the total feed with a preferred range of more than 5 up to about 15 volume percent. In general at least 6 volume percent of the aldehyde is used in the feed. The corresponding ranges for oxygen are 3 to 15 volume percent, preferably 5 to 12 volume percent and for steam up to 50 volume percent, preferably 5 to 35 volume percent, the balance being the inert gas or gases.

The temperature of the reaction should, for best results, be within the range of from about 270° to 450° C., preferably 280°-400° C., and the optimum temperature range is 290° to 325° C. Because the reaction is exothermic, means for conducting the heat away from the reactor are normally employed to avoid a temperature increase which favors the destruction of methacrolein by complete oxidation to carbon oxides and water. The reactor temperature may be controlled by conventional methods such as by surrounding the catalyst-containing tubes with a molten salt bath.

The reaction may be conducted at atmospheric, superatmospheric or subatmospheric pressure. Preferably, however, pressures are employed ranging from atmospheric up to about 8 kg/cm² absolute, preferably up to about 6.3 kg/cm² absolute, and most preferably up to about 4.5 kg/cm² absolute.

The unsaturated acid product may be recovered by a number of methods well known to those skilled in the art. For example, the acid may be condensed, or scrubbed with water or other suitable solvents, followed by separation of the unsaturated acid product from the scrubbing liquid. The gases remaining after the acid-removal step may be recycled to the reaction preferably after removal of $CO_2$ by conventional means, e.g., absorption in aqueous carbonate solution.

The features of the invention will be more readily apparent from the following specific examples of typical catalyst preparation and its use in the oxidation of methacrolein. It will be understood, however, that these examples are for the purpose of illustration only and are not to be interpreted as limiting the invention.

EXAMPLE 1

Catalyst Preparation

In 750 cc of water are dissolved 636 grams of $(NH_4)_6Mo_7O_{24}\cdot 4H_2O$. Then 21.7 grams of $Cu(NO_3)_2\cdot 3H_2O$ are dissolved in 100 cc of water, 58.4 grams of $CsNO_3$ are dissolved in 150 cc of water, 20.5 grams of $SbCl_3$ are dissolved in a mixture of 30 cc of water, and 10 cc of concentrated HCl and 34.5 grams of $H_3PO_4$ are dissolved in a mixture of 100 cc of water and 50 cc of 58% $NH_4OH$ solution. These solutions are mixed with 400 cc of 58% $NH_4OH$ and fed to a rotary dryer of 4000 cc capacity and the mixture is evaporated to dryness at a temperature reaching a maximum of 140°-200° C. The resulting powder is removed from the dryer and dried in an oven at 200° C. for 4 hours. The dried powder is screened through a 20-mesh screen, a 4% aqueous solution of polyvinyl alcohol is added in sufficient quantity to make a damp mixture and this mixture is dried at 75°-80° C. until the moisture content falls to 2-4 wt.%. The dried mixture is then screened to 20-60 mesh size particles, and about 2-6% of stearic acid powder is thoroughly mixed with it. The resulting mixture is then pelletized to form pellets of 3/16 inch height and diameter in which the catalyst components molybdenum, copper, phosphorus, antimony, cesium are present (by calculation) in the atomic ratios of 12, 0.3, 1, 0.3 and 1, respectively. The pellets are then activated in an oven by heating them to 100° C. in one hour and then raising the temperature gradually at a rate of about 20° C. per hour to 370° C. and maintaining them at this temperature for 8 hours. The catalyst is tested according to the procedure of Example 2.

EXAMPLE 2

Catalyst Testing

A 150 cc quantity of the catalyst composition of Example 1 is placed in a reactor defined by a ½"×90" stainless steel pipe, the reactor pipe being filled with 50 cc of inert filler (silicon carbide) below the catalyst bed and 100 cc of the inert filled above the catalyst bed in conventional manner to insure uniform temperature contact with the catalyst. Nitrogen-diluted mixtures containing methacrolein, oxygen and steam are fed to the reactor at a pressure of 1.74 kg/cm² (absolute) and at a space velocity of about 1200 hr$^{-1}$. The term "space velocity" is used in its conventional sense to mean liters of gas (at standard temperature and pressure) per liter of catalyst per hour. The feed composition is approximately, by volume, 6-7% methacrolein, 11-12% oxygen and 20% steam, the balance being nitrogen, determination being made on a wet basis. The reaction is run continuously and the exit gas is analyzed at intervals of several hours. Analyses are carried out by means of gas chromatography and by infrared spectrography using conventional techniques. The average amount of methacrylic acid produced is determined periodically and the reactor temperature is adjusted as necessary to obtain the desired yield, that is, the product of the conversion and the selectivity, which for purposes of the comparisons to be made is about 0.15 gm of methacrylic acid per hour per gram of catalyst.

EXAMPLE 3

A catalyst is prepared according to the method of Example 1 except that the phosphorus content is increased to provide a catalyst having the following nominal composition (by calculation):

$$Mo_{12}Cu_{0.3}P_{1.5}Sb_{0.3}Cs_1O_x$$

The catalyst is tested according to the method of Example 2.

EXAMPLE 4

A catalyst is prepared according to the method of Example 1 but having a higher phosphorus content than the catalyst of Example 3, providing a catalyst having the following nominal composition (by calculation):

$$Mo_{12}Cu_{0.3}P_2Sb_{0.3}Cs_1O_x$$

The catalyst is tested according to the method of Example 2.

The results of the tests carried out on the catalysts of Examples 1, 3, and 4 are summarized in the following Table I.

TABLE I

| Cat. | Phosphorus Content[a] | Hours | Temp. °C. | Selectivity to Methacrylic Acid[b] | Activity Coeff. K[c] |
|---|---|---|---|---|---|
| 1 | 1 | 35 | 293 | 77 | 23 |
|   |   | 80 | 323 | 74.5 | 6 |
| 3 | 1.5 | 150 | 298 | 77.6 | 26 |
|   |   | 200 | 296 | 79.7 | 26 |
| 4 | 2 | 26 | 320 | 70 | 10 |
|   |   | 122 | 324 | 65 | 7 |

[a] relative to $Mo_{12}$
[b] percent of methacrolein reacted which is converted to methacrylic acid
[c] a value calculated from experimental data to provide a measure of catalyst activity and derived from the equation:
$K = F \cdot X \cdot S \cdot C^{E/RT}$ where:
F = methacrolein concentration in feed
S = space velocity of feed gas
X = conversion of methacrolein
E = activation energy, 25,000 k cal/mol.
R = gas constant
T = absolute temperature As explained in Example 2 the catalysts are operated to provide a constant predetermined yield of methacrylic acid. In order to provide a proper comparison, the performance of a catalyst is reported at the period of time where the catalyst activity has stabilized after an initial break-in period. This may mean, as in Table I, that the time selected for comparisons is not the same if the catalyst performance differs significantly. A stable period at 150-200 hours could be established readily for the catalyst of Example 3, while the catalysts of Examples 1 and 4 had relatively poorer performance and their activities declined earlier, as indicated by the data. It is clear that the catalyst of Example 3 is superior to those of Examples 1 and 4, since it operated consistently at a lower temperature and with higher activity and selectivity after the other catalysts had lost significant activity. Thus, is is concluded that catalysts containing molybdenum, copper, antimony, and cesium are sensitive to the phosphorus content. An optimum level should be found between a phosphorus level of 1 and 2 (relative to $Mo_{12}$). It is believed that the optimum level is located between $P_{1.2}$ and $P_{1.8}$, particularly between $P_{1.3}$ and $P_{1.7}$.

EXAMPLE 5

A catalyst corresponding to that of Example 1 is prepared by the same general technique except that 5 grams of perrhenic acid dissolved in 100 cc of water are included in the initial solution to provide rhenium in a catalyst having the following nominal composition (by calculation):

$Mo_{12}Cu_{0.3}P_1Sb_{0.3}Cs_1Re_{0.07}O_x$

EXAMPLE 6

A catalyst is prepared according to the general method of Example 5 except that the amount of phosphorus is increased to produce a catalyst having the following nominal composition (by calculation).

$Mo_{12}Cu_{0.3}P_{1.5}Sb_{0.3}Cs_1Re_{0.07}O_x$

The catalyst is tested according to the methods of Example 2.

EXAMPLE 7

A catalyst is prepared according to the method of Example 5 but the amount of phosphorus is doubled to provide a catalyst having the following nominal composition (by calculation):

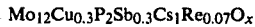
$Mo_{12}Cu_{0.3}P_2Sb_{0.3}Cs_1Re_{0.07}O_x$

The catalyst is tested according to the procedures of Example 2.

The results of testing the catalysts of Examples 5, 6, and 7 are summarized in the following Table II, to which the footnotes of Table I also apply.

TABLE II

| Cat. | Phosphorus Content(a) | Hours | Temp. °C. | Selectivity to Methacrylic Acid(b) | Activity Coeff. K (c) |
|---|---|---|---|---|---|
| 5 | 1 | 150 | 292 | 75 | 26 |
|   |   | 200 | 293 | 75.5 | 26 |
| 6 | 1.5 | 150 | 279 | 77 | 46.6 |
|   |   | 250 | 279 | 77 | 40 |
| 7 | 2 | 150 | 311 | 73.6 | 11.6 |
|   |   | 250 | 311 | 76 | 12 |

As in Table I, the catalysts are operated to provide the same yield of methacrylic acid and the performance is reported during a stable period of operation after the initial break-in of the catalyst. It will be clear that the catalysts having rhenium added have better performance than those of Table I, which contain no rhenium, since they have higher activity and suggest improved aging characteristics, especially with respect to the comparison of catalysts 5 and 7 with catalysts 1 and 4. The rhenium-containing catalysts also are sensitive to the phosphorus content and an optimum value again appears between $P_1$ and $P_2$ (relative to $Mo_{12}$). It is believed that the optimum value is between $P_{1.2}$ and $P_{1.8}$, particularly between $P_{1.3}$ and $P_{1.7}$.

Taking the results of Tables I and II together, it may be concluded that the ratio of molybdenum to phosphorus for catalysts of this type will show an optimum performance at ratios between 12/1 to 12/2.

EXAMPLE 8

A catalyst is prepared according to the general method of Example 1 except that 79.2 gms of $Ca(C_2H_3O_2)_2 \cdot X H_2O$ are substituted for cesium nitrate and no aqueous ammonia is added and a catalyst having the following nominal composition (by calculation) is produced:

$Mo_{12}Cu_{0.3}P_1Sb_{0.3}Ca_{1.5}O_x$

This catalyst is tested according to the methods of Example 2 and the significance of the phosphorus to molybdenum ratio to catalyst performance is shown. The catalyst is operated at about 304° C. for a period between about 20 to 80 hours with a selectivity of 76.3 and an activity coefficient of 18.6.

EXAMPLE 9

A catalyst is prepared according to Example 8 except that 5 grams of $Re_2O_7$ dissolved in 100 cc of water is included in the solution to provide rhenium a catalyst having the following nominal composition (by calculation):

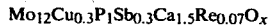
$Mo_{12}Cu_{0.3}P_1Sb_{0.3}Ca_{1.5}Re_{0.07}O_x$

The catalyst is tested according to the method of Example 2. The significance of the phosphorus to molybdenum ratio to catalyst performance is shown. The catalyst is operated at about 286° C. for a period between about 30 to 200 hours with a selectivity of 75.2 and an activity coefficient of 42.

EXAMPLE 10

A catalyst is prepared according to the general method of Example 9 except that instead of rhenium, tungsten is included and no aqueous ammonia is used to provide a catalyst having the following nominal composition (by calculation):

$$Mo_{12}Cu_{0.3}P_1Sb_{0.3}Ca_1W_{0.5}O_x$$

The catalyst is tested according to the method of Example 2 and the significance of the phosphorus to molybdenum ratio to catalyst performance is shown. For a period between about 20 to 170 hours the catalyst is operated at about 302° C., with a selectivity of about 76.5 and an activity coefficient of about 22.4.

EXAMPLE 11

A catalyst is prepared according to the general method of Example 1 except that the phosphorus level is increased and palladium is included to produce a catalyst having the following nominal composition:

$$Mo_{12}Cu_{0.3}P_2Sb_{0.3}Cs_1Pd_{0.03}O_x$$

The catalyst is tested under the conditions of Example 2 and the significance of the phosphorus to molybdenum ratio with respect to catalyst performance is shown.

EXAMPLE 12

A catalyst is prepared according to the general method of Example 1 except that the phosphorus level is increased and rubidium is added to produce a catalyst having the following nominal composition:

$$Mo_{12}Cu_{0.3}P_{1.75}Sb_{0.3}Cs_{0.5}Rb_{0.5}O_x$$

The catalyst is tested under the conditions of Example 2 and the significance of the phosphorus to molybdenum ratio with respect to catalyst performance is shown.

EXAMPLE 13

Other suitable catalysts in accordance with the invention are prepared according to the general method of Example 1 and have the following nominal compositions:

$Mo_{12}Cu_{0.3}P_2Sb_{0.3}Cs_{0.3}Ca_{0.7}Cr_{0.3}O_x$
$Mo_{12}Cu_{0.3}P_2Sb_{0.3}Cs_{0.3}K_{0.7}V_{0.3}O_x$
$Mo_{12}Cu_{0.3}P_2Sb_{0.3}Cs_{0.3}Sr_{0.7}Nb_{0.3}O_x$
$Mo_{12}Cu_{0.3}P_{1.7}Sb_{0.3}Cs_{0.3}Ba_{0.7}Mn_{0.3}O_x$
$Mo_{12}Cu_{0.3}P_{1.2}Sb_{0.3}Cs_1La_{0.7}Ni_{0.3}O_x$
$Mo_{12}Cu_{0.3}P_1Sb_{0.3}Cs_{0.3}Ce_{0.7}Zn_{0.3}O_x$
$Mo_{12}Cu_{0.3}P_1Sb_{0.3}Cs_1Ru_{0.1}O_x$
$Mo_{12}Cu_{0.3}P_{0.5}Sb_{0.3}Cs_1Rh_{0.03}O_x$
$Mo_{12}Cu_{0.3}P_1Sb_{0.3}Cs_{0.3}Pt_{0.03}O_x$
$Mo_{12}Ca_{0.3}P_{1.5}Sb_{0.3}Cs_1W_{0.5}$

The catalysts are tested under the conditions of Example 2 and the significance of the phosphorus to molybdenum ratio with respect to catalyst performance is shown.

What is claimed is:

1. A catalyst suitable for the vapor-phase oxidation of methacrolein to methacrylic acid consisting essentially of the composition expressed by the formula:

$$Mo_{12}Cu_aP_bSb_cA_dB_eO_x$$

where: $a=0.05-3$; $b=0.1-5$; $c=0.01-3$; $d=0.1-3$; $e=0.01-3$; and $x=a$ value determined by the valence and proportions of the other elements of the formula, where A is Cs and/or Ca and B is one more elements selected from the group consisting Ni, Zn, Ru, Rh, Pd, Pt, As, K, Rb, Sr, Ba, Cr, V, Nb, W, Mn, Re, and rare earth metals including La.

2. A catalyst of claim 1 wherein $b=1-2$.
3. A catalyst of claim 2 wherein $b=1.2-1.8$.
4. A catalyst of claim 1 wherein A is Cs.
5. A catalyst of claim 4 wherein $b=1.2-1.8$.
6. A catalyst of claim 5 wherein $b=1.3-1.7$.
7. A catalyst of claim 1 where A is Ca.
8. A catalyst of claim 7 wherein $b=1-2$.
9. A catalyst of claim 8 wherein $b=1.2-1.8$.
10. A catalyst suitable for the vapor-phase oxidation of methacrolein to methacrylic acid consisting essentially of the composition expressed by the formula:

$$Mo_{12}Cu_aP_bSb_cCs_dO_x$$

where: $a=0.05-3$; $b=1-2$; $c=0.01-3$; $d=0.1-3$; and $x=a$ value determined by the valence and proportions of the other elements of the formula.

11. A catalyst of claim 10 wherein $b=1.2-1.8$.
12. A catalyst of claim 11 wherein $b=1.3-1.7$.
13. A catalyst suitable for the vapor-phase oxidation of methacrolein to methacrylic acid consisting essentially of the composition expressed y the formula:

$$Mo_{12}Cu_aP_bSb_cCa_dO_x$$

where: $a=0.05-3$; $b=1-2$; $c=0.01-3$; $d=0.1-3$; and $x=a$ value determined by the valence and proportions of the other elements of the formula.

14. A catalyst suitable for the vapor-phase oxidation of methacrolein to methacrylic acid consisting essentially of the composition expressed by the formula:

$$Mo_{12}Cu_aP_bSb_cCs_dRe_eO_x$$

where: $a=0.05-3$; $b=1-2$; $c=0.01-3$; $d=0.1-3$; $e=0.005-0.5$; and $x=a$ value determined by the valence and proportions of the other elements of the formula.

15. A catalyst of claim 14 wherein $b=1.2-1.8$.
16. A catalyst of claim 15 wherein $b=1.3-1.7$.
17. A catalyst suitable for the vapor-phase oxidation of methacrolein to methacrylic acid consisting essentially of the composition expressed by the formula:

$$Mo_{12}Cu_aP_bSb_cCa_dRe_eO_x$$

where: $a=0.05-3$; $b=1-2$; $c=0.01-3$; $d=0.1-3$; $e=0.005-0.5$; and $x=a$ value determined by the valence and proportions of the other elements of the formula.

18. A catalyst suitable for the vapor-phase oxidation of methacrolein to methacrylic acid consisting essentially of the composition expressed by the formula:

$$Mo_{12}Cu_aP_bSb_cCa_dW_eO_x$$

where: $a=0.05-3$; $b=1-2$; $c=0.01-3$; $d=0.1-3$; $e=0.01-3$; and $x=a$ value determined by the valence and proportions of the other elements of the formula.

19. The catalyst of claim 18 further comprising arsenic.

* * * * *

UNITED STATES PATENT AND TRADEMARK OFFICE
CERTIFICATE OF CORRECTION

PATENT NO. : 4,271,040

DATED : June 2, 1981

INVENTOR(S) : Sargis Khoobiar

It is certified that error appears in the above-identified patent and that said Letters Patent is hereby corrected as shown below:

Column 10, line 7, after "one" insert --or--.

Column 10, line 7, after "more" insert --of the--.

Signed and Sealed this

Twenty-sixth Day of December, 1989

Attest:

JEFFREY M. SAMUELS

Attesting Officer

Acting Commissioner of Patents and Trademarks